United States Patent
Lee et al.

(10) Patent No.: US 7,098,018 B2
(45) Date of Patent: Aug. 29, 2006

(54) **AMINOPEPTIDASE DERIVED FROM *BACILLUS LICHENIFORMIS*, GENE ENCODING THE AMINOPEPTIDASE, EXPRESSION VECTOR CONTAINING THE GENE, TRANSFORMANT AND METHOD FOR PREPARATION THEREOF**

(75) Inventors: Young-Phil Lee, Daejeon (KR); Seung-won Lee, Seongnam-si (KR); Chul-ho Jung, Daejeon (KR); Hyung-Cheol Kim, Daejeon (KR); Soon-Yong Choi, Daejeon (KR); Jin-suk Kim, Daejeon (KR); Hyun-Sik Kim, Daejeon (KR); Jung-Woo Seo, Seoul (KR)

(73) Assignee: LG Life Sciences Ltd., Seoul (KR)

( * ) Notice: Subject to any disclaimer, the term of this patent is extended or adjusted under 35 U.S.C. 154(b) by 157 days.

(21) Appl. No.: 10/481,531

(22) PCT Filed: Jul. 6, 2002

(86) PCT No.: PCT/KR02/01280

§ 371 (c)(1),
(2), (4) Date: Dec. 19, 2003

(87) PCT Pub. No.: WO03/004635
PCT Pub. Date: Jan. 16, 2003

(65) Prior Publication Data
US 2004/0253703 A1    Dec. 16, 2004

(30) Foreign Application Priority Data
Jul. 6, 2001    (KR) .................... 2001-40268
May 31, 2002    (KR) .................... 2002-30798

(51) Int. Cl.
*C12N 9/56* (2006.01)
*C12N 15/57* (2006.01)
*C12N 15/74* (2006.01)
*C12P 21/06* (2006.01)

(52) U.S. Cl. .................. 435/222; 435/68.1; 435/69.1; 435/252.3; 435/320.1; 536/23.2

(58) Field of Classification Search .................. None
See application file for complete search history.

(56) References Cited

U.S. PATENT DOCUMENTS

| | | | |
|---|---|---|---|
| 4,755,465 A | | 7/1988 | Gray et al. |
| 5,112,812 A | * | 5/1992 | Samuelsson et al. ......... 514/21 |
| 5,126,249 A | | 6/1992 | Becker et al. |
| 6,428,997 B1 | * | 8/2002 | Lee et al. .................. 435/212 |
| 2002/0146721 A1 | * | 10/2002 | Berka et al. .................. 435/6 |

FOREIGN PATENT DOCUMENTS

| | | |
|---|---|---|
| WO | WO 89/12678 | 12/1989 |
| WO | WO 98/38290 A1 * | 9/1998 |

* cited by examiner

*Primary Examiner*—Nashaat T. Nashed
*Assistant Examiner*—William W. Moore
(74) *Attorney, Agent, or Firm*—Swanson & Bratschun, L.L.C.

(57) ABSTRACT

The present invention relates to novel aminopeptidase derived from *Bacillus licheniformis*, a gene encoding the aminopeptidase, an expression vector containing the gene, a cell transformant transfected with the expression vector and a process for preparing a natural type protein using thereof. More particularly, the present invention relates to a gene encoding aminopeptidase which is cloned and manufactured using the recombinant DNA technique, an expression vector containing the gene, a cell transformant transfected with the expression vector and a recombinant aminopeptidase which is necessary to produce recombinant human growth hormone in a natural type protein and can be expressed in a high yield more stably and advantageously, compared with conventional methods for the purification.

8 Claims, 4 Drawing Sheets

FIG. 1

| | Amino acid sequence of peptides seperated through reverse phase chromatography after trypsine treatment | | | | | | | | |
|---|---|---|---|---|---|---|---|---|---|
| | T4 | T6 | T7 | T9 | T11 | T13 | T14 | T16 | T17 |
| 1 | I(>H) | H,A(>D) | D,T,H | H(>D,A) | K,D,H | D,G,H | D,H,F | H,A,D | D,H,A |
| 2 | M(>Y) | Y | A | Y | A | V | I | – | A or – |
| 3 | K(>V) | Q | G | Q | K | K | T | – or S(>L) | – or S,K |
| 4 | T(>S) | T | O | T | G | N | F | L | L |
| 5 | V | I | I | I | V | P | G | – or S,V | – or S,V |
| 6 | P(>L) | Y | A | Y | K | D | A | L | L |
| 7 | A(>S) | H | G | H(?) | N | I(>N) | E | G | G |
| 8 | D(>E) | L | T | L | P | V | – or E | K | K |
| 9 | K(>Q) | S | A | S(>A) | D | Y | I | D | D |
| 10 | E | E | V | E | I | V | G | V | V |
| 11 | I(>V) | T | Y | T | V | Q | L | L | L |
| 12 | K(>R) | V | N | V | Y | S,Y | L | F | F |
| 13 | – or R | G | L | Q | V | R(>Q) | G | L | L |
| 14 | | P | T | P | T | Y | S | H | H |
| 15 | | R | K | R | S | D | R | Q | Q |
| 16 | | – | K or – | V | H | – or S | H | G | G |
| 17 | | Q(?) | E | T | Y | V | Y | G | G or – |
| 18 | | | N | G | D | P(>L) | V | S | S |
| 19 | | | R(?) | – or T | S | Y | S | S or – | S or – |
| 20 | | | T | A | V | A | T | D | D |
| 21 | | | P | E | | | | | |
| 22 | | | S | E | | | | | |
| 23 | | | | K | | | | | |
| 24 | | | | K | | | | | |
| 25 | | | | S or – | | | | | |
| 26 | | | | A | | | | | |
| 27 | | | | A or – | | | | | |
| Character denoted as '–' may be a cystein residue or modified amino acid | | | | | | | | | |

US 7,098,018 B2

AMINOPEPTIDASE DERIVED FROM BACILLUS LICHENIFORMIS, GENE ENCODING THE AMINOPEPTIDASE, EXPRESSION VECTOR CONTAINING THE GENE, TRANSFORMANT AND METHOD FOR PREPARATION THEREOF

RELATED APPLICATIONS

This application is a 35 U.S.C. § 371 national phase application of PCT/KR02/01280 (WO 03/004635) filed on Jul. 6, 2002, entitled "Novel Aminopeptidase Derived from *Bacillus Licheniformis*, Gene Encoding the Aminopeptidase, Expression Vector Containing the Gene, Transformant and Method for Preparation Thereof" which claims priority to Korean Application No. 2001-0040268, filed Jul. 6, 2001 and Korean Application No. 2002-0030798, filed May 31, 2002, both of which are incorporated herein by reference in their entirety.

TECHNICAL FIELD

The present invention relates to novel aminopeptidase derived from *Bacillus licheniformis*, a gene encoding the aminopeptidase, an expression vector containing the gene, a cell transformant transfected with the expression vector and a process for preparing a natural type protein using thereof. More particularly, the present invention relates to a gene encoding aminopeptidase which is cloned and manufactured using the recombinant DNA technique, an expression vector containing the gene, a cell transformant transfected with the expression vector and a recombinant aminopeptidase which is necessary to produce recombinant human growth hormone in a natural type protein and can be expressed in a high yield more stably and advantageously, compared with conventional methods for the purification.

BACKGROUND ART

Generally, recombinant proteins are made as non-natural types when they are expressed in a large scale through the gene manipulation in microbes. In detail, most of the recombinant proteins having a initiator, methionine(MET), in the amino terminus, which were treated inappropriately are produced. The recombinant proteins containing methionine at the amino terminus might induce immunogenic reactions or become being unstable so as not to play an intrinsic role of the protein, in case of being administered to human or other animals. Therefore, it is very important to develop a new method for preparing such a recombinant protein as its natural type protein (See Nature, 1987, 326, 315; J. Bacteriol., 1987, 169, 751–757; *Bio/Technology*, 1990, 8, 1036–1040; *Appl. Microbiol. Biotechnol.*, 1991, 36, 211–215).

Human growth hormone is a polypeptide hormone which has 22,125 Da of molecular weight, contains a sequence of Phe-Pro-Thr at the amino terminus and is composed of 191 amino acids secreted from human pituitary gland and mostly has been applied to treat pituitary dwarfism (See Raben, M. S., J. Clin. Endocr., 1958, 18, 901). Up to now, human growth hormone has been extracted and purified from pituitary glands of the dead, but is hard to be provided for all the patients due to the limited supply. Recently, several studies regarding expression and separation of the human growth hormone from *Escherichia coli*, yeast and the like by gene manipulation have been performed. Actually, the human growth hormone produced through the DNA technology has been used for clinical applications (in case of *Escherichia coli*, See Korean Patent Publication No. 89-1244 and No. 87-701; Korean Patent Laid-open No. 87-2258 and No. 84-8695; in case of yeast, See Korean Patent Publication No. 92-99; Korean Patent Laid-open No. 90-9973 and No. 90-9976).

However, if a human growth hormone is produced by using the recombinant DNA technology described above, one methionine residue, an initiation codon for protein synthesis is bound additionally at the amino terminus except 191 amino acid residues consisting in a natural type human growth hormone and thus a methionyl human growth hormone which is started from the sequence of Met-Phe-Pro-Thr of the amino terminus and composed of 192 amino acid residues is produced. The methionyl human growth hormone has the same biological activities as that of the natural type of human growth hormone (Moore, J. A., Endocrinology, 1988, 122, 2920–2926) and is not reported yet to provoke side effects by presence of the methionine at the amino terminus. However, antibodies might be generated on rare occasions due to the methionine and are reported to be produced in a higher ratio than those from the natural type hormone (Lancet, 1986, Mar. 29, 697).

Hence, there are several approaches to produce a natural type hormone which do not contain the methionine. Concretely, the human growth hormone is produced by one method in which the amino terminus is fused with the carboxy terminus of another protein; and then digested by using a specific protease (See PCT International Application WO 89/12678; European Patent Application EP 20209; European Patent EP 321940); and by another method which comprises (1) expressing growth hormone within cells; (2) digesting methionine while secreted out of host cells; and (3) obtaining a natural type human growth hormone from culture media (See European Patent EP 008832; U.S. Pat. No. 4,755,465; Japanese Patent JP 01273591; European Patent Application EP 306673; Korean Patent Application No. 92-10932). But, there are some disadvantages in these methods illustrated above. Precisely, it is required of complicating construction a new expression vectors and steps of transforming host cells and coincidently to optimize the expression conditions with extra trials.

On the other hand, in case that exogenous protein produced by using recombinant DNA technologies include an extra amino acid at the amino terminus, the aminopeptidase can be exploited to remove the extra amino acid and as a result, the exogenous protein having the same structure with the natural type protein can be yielded easily. Concretely, specific aminopeptidase which cuts selectively only methionine residue present at the amino terminus of the methionyl human growth hormone purified through conventional methods can be used in order to produce a natural type human growth hormone (See PCT International Application WO 86/04609 and WO 86/204527 A1).

Presently, various kinds of aminopeptidases have been demonstrated to prepare a natural type human growth hormone. In detail, the aminopeptidase purified from Aeromonas proteolytica (See PCT International Application WO 86/01229; European Patent EP 0489711, A3, BTG company; Prescott and Wilks, Method in Enzymology, 1976, 44, 530–543), the aminopeptidase purified from porcine kidney (See PCT International Application WO 86/204527 A1; Bio/Technology, 1987, 5, 824–827, Takeda company), the dipeptidyl aminopeptidase purified from Dictyostelium discoidium (See European Patent EP 557076; U.S. Pat. No. 5,126,249, A1, Eli Lilly company), and the aminopeptidase from Streptomyces thermonitripican were reported.

In order to attain the above object, the aminopeptidase should not work on the amino acid sequence of a natural type protein although it removes unnecessary amino acid residues present at the amino terminus of the recombinant protein. Namely, when the original protein has a amino acid sequence starting from X-Y-Z at the amino terminus and the recombinant protein has the amino acid sequence of Met-X-Y-Z-containing an additional methionine at the amino terminus, the aminopeptidase should cut only the methionine residue and not work onto other amino acids (X-Y-Z-) afterward so as to produce the recombinant protein having the same amino acid sequence as that of the natural type protein. Therefore, the aminopeptidase satisfying such an object should be compatible in its substrate specificity depending upon the target protein for industrial applications. Although the enzyme has such a characteristic, it is advantageous to have higher intrinsic activities itself.

Presently, more than several tens of aminopeptidases have been extracted from microbes and the like and disclosed. In common, most enzymes need metal ions such as calcium, zinc or the like in order to be activated. These aminopeptidases have various properties in view of molecular weight, essential metal ions, optimal condition of the reaction, substrate specificity and so on according to microbes, although they have common activities in view of the digestion in amino acid residues at the amino terminus of the protein (See FEMS Microbiol. Rev., 1996, 18, 319–344). Such an aminopeptidase is classified to an exopeptidase and has a property to isolate a amino acid from the amino terminus of substrate protein in orders.

Precisely, these aminopeptidases have been reported and separated, especially from *Bacillus* sp., for example *Bacillus subtilis* (See Arch. Biochem. Biophys., 1979, 197, 63–77; Arch. Biochem. Biophys., 202, 540–545, 1980; J. Biochem., 1994, 107, 603–607; Japanese Patent JP 03285684, Diacel-Chem company), *Bacillus stearothermophilus* (See Meth. Enzymol., 1970, 19, 544–552; Biochem. Biophys. Acta, 1976, 438, 221–220; European Patent EP 101653, Unitika company), *Bacillus thuringensis* (*Biokhimiya*, 1984, 49, 1899–1907), *Bacillus licheniformis* (*Arch. Biochem. Biophys.*, 1978, 186, 383–391; *Mikrobiol. Zh.*, 1989, 51, 49–52) and so on.

In the references mentioned above, the aminopeptidases are purified and analyzed for their enzymatic properties by using leucine-p-nitroanilide, and several dipeptides or the like as a substrate. However, oligopeptides starting from the sequence of Met-X-Pro at the amino termini or proteins starting from Met-X-Pro at the amino termini are not used as a substrate in order to measure enzymatic activities. Therefore, it is not verified yet that these aminopeptidases might be applied to the methionine removal in recombinant proteins containing Met-X-Pro sequence at their amino termini.

Furthermore, the aminopeptidases derived from *Bacillus licheniformis* have been illustrated as follows. Rodriguez et al. have purified the aminopeptidase derived from *Bacillus licheniformis* ATCC 12759 and examined its enzymatic property. Also, the inventors of the present invention have disclosed the method for preparing a natural type human growth hormone using the aminopeptidase derived from *Bacillus licheniformis*, the characterization of the purified aminopeptidase in its enzymatic properties and its amino acid sequence at the amino terminus (Korean Patent Laid-open No. 1998-071239). In this invention, for producing a natural type protein in a large scale through recombinant DNA technologies, the inventors of the present invention have reported that the aminopeptidase could remove only methionine residue in synthetic substrates, oligopeptides, proteins and the like and recognize the specific amino acid sequence of Met-X-Pro (hereinafter, X denotes any amino acid regardless of its kind) and thus be suitable for the production of the natural type human growth hormone (Korean Patent Laid-open No. 1998-071239). These conventional methods have elucidated that the aminopeptidase can be produced from *Bacillus licheniformis* and exploited to produce a natural type recombinant protein. Besides, they have provided only the information about the partial amino acid sequence of the amino terminus and the total gene of aminopeptidase has not determined yet.

Hence, the inventors of the present invention have tried to obtain novel aminopeptidase for producing a natural type recombinant protein. Concretely, we have cloned a gene of aminopeptidase derived from *Bacillus licheniformis*, determined its nucleotide sequence and amino acid sequence and expressed the cloned aminopeptidase gene in recombinant bacterial strains. Then, the recombinant protein was identified to have aminopeptidase activities, to be useful for use easily other enzymatic reaction as well as the preparation of natural type proteins. Consequently, the present invention has been completed successfully.

DISCLOSURE OF INVENTION

The object of the present invention is to provide novel aminopeptidase derived from *Bacillus licheniformis*, a gene encoding the aminopeptidase, an expression vector containing the gene, a cell transformant transfected with the expression vector and a process for preparing a natural type protein using thereof, which can be used to manufacture a recombinant protein as well as applied to other enzymatic reactions usefully.

In order to accomplish the object described above, the present invention provides an aminopeptidase derived from *Bacillus licheniformis*.

Precisely, the aminopeptidase has an amino acid sequence selected from the group comprising the amino acid sequence having the full length of SEQ. ID NO: 1 or an amino acid sequence selected from a sequence which comprises the amino acid of SEQ. ID NO: 1 having a deletion of one or more amino acids.

Preferably, the aminopeptidase has an amino acid sequence selected from the group comprising the amino acid sequence of SEQ ID NO:1 having a deletion of one or more amino acids at the amino terminus, carboxy terminus or both termini.

More preferably, the aminopeptidase is selected from a group of aminopeptidases having a deletion at the amino terminus of SEQ ID NO:1 wherein said amino acid sequence is selected from the group consisting of: an amino acid sequence having a deletion of amino acids 1 through 30 of SEQ. ID NO: 1; an amino acid sequence having a deletion of amino acids 1 through 39 of SEQ. ID NO: 1; an amino acid sequence having a deletion of amino acids 1 through 40 of SEQ. ID NO: 1; an amino acid sequence having a deletion of amino acids 1 through 41 of SEQ. ID NO: 1; and an amino acid sequence having a deletion of amino acids 1 through 42 of SEQ. ID NO: 1. In addition the aminopeptidase is selected from the group consisting of the above referenced sequences having a further deletion of amino acids 444 through 449 at the carboxy terminus of SEQ ID NO:1.

In addition, the aminopeptidase has the amino acid sequence of SEQ. ID NO: 1 having a deletion of amino acids 444 through 449 at the carboxy terminus.

In addition, the present invention provides a gene encoding the aminopeptidase derived from *Bacillus licheniformis*.

Precisely, the gene encoding the aminopeptidase has a nucleotide sequence that encodes an aminopeptidase selected from the group consisting of SEQ ID NO:1, or a fragment thereof wherein said fragment is selected from the group consisting of: an amino acid sequence having a deletion of amino acids 1 through 30 of SEQ. ID NO: 1; an amino acid sequence having a deletion of amino acids 1 through 39 of SEQ. ID NO: 1; an amino acid sequence having a deletion of amino acids 1 through 40 of SEQ. ID NO: 1; and an amino acid sequence having a deletion of amino acids 1 through 41 of SEQ. ID NO: 1; an amino acid sequence having a deletion of amino acids 1 through 30 and 444 through 449 of SEQ. ID NO: 1; an amino acid sequence having a deletion of amino acids 1 through 39 and 444 through 449 of SEQ. ID NO: 1; an amino acid sequence having a deletion of amino acids 1 through 40 and 444 through 449 of SEQ. ID NO: 1; and an amino acid sequence having a deletion of amino acids 1 through 41 and 444 through 449 of SEQ. ID NO: 1 and an amino acid sequence having a deletion of amino acids 444 through 449 of SEQ ID NO:1.

In addition, the present invention provides an expression vector pLAP132 which contains the gene encoding the aminopeptidase with the nucleotide sequence in the full length of SEQ. ID NO: 2.

Besides, the present invention provides an *Escherichia coli* transformant XLOLR/LAP132 which is transfected with the expression vector pLAP132 (accession number: KCTC 1000 BP).

Furthermore, the present invention provides a process for preparing a peptide or protein having a native amino-terminus lacking a methionine amino acid which comprises the following steps: (1) purifying a recombinant protein containing a methionine-X-proline sequence at the amino terminus; (2) adding an aminopeptidase to said purified recombinant protein; and (3) digesting said mixture thereby obtaining said protein or peptide having a native amino-terminus lacking a methionine amino acid.

At this moment, X of the Met-X-Pro can be any kind of amino acid.

BRIEF DESCRIPTION OF THE DRAWINGS

The above and other objects, features and other advantages of the present invention will be more clearly understood from the following detailed description taken in conjunction with the accompanying drawings, in which;

FIG. 1 depicts the determination of amino acid sequences in peptide fragments of the aminopeptidase obtained after treating trypsin.

BEST MODE FOR CARRYING OUT THE INVENTION

Figure 2:
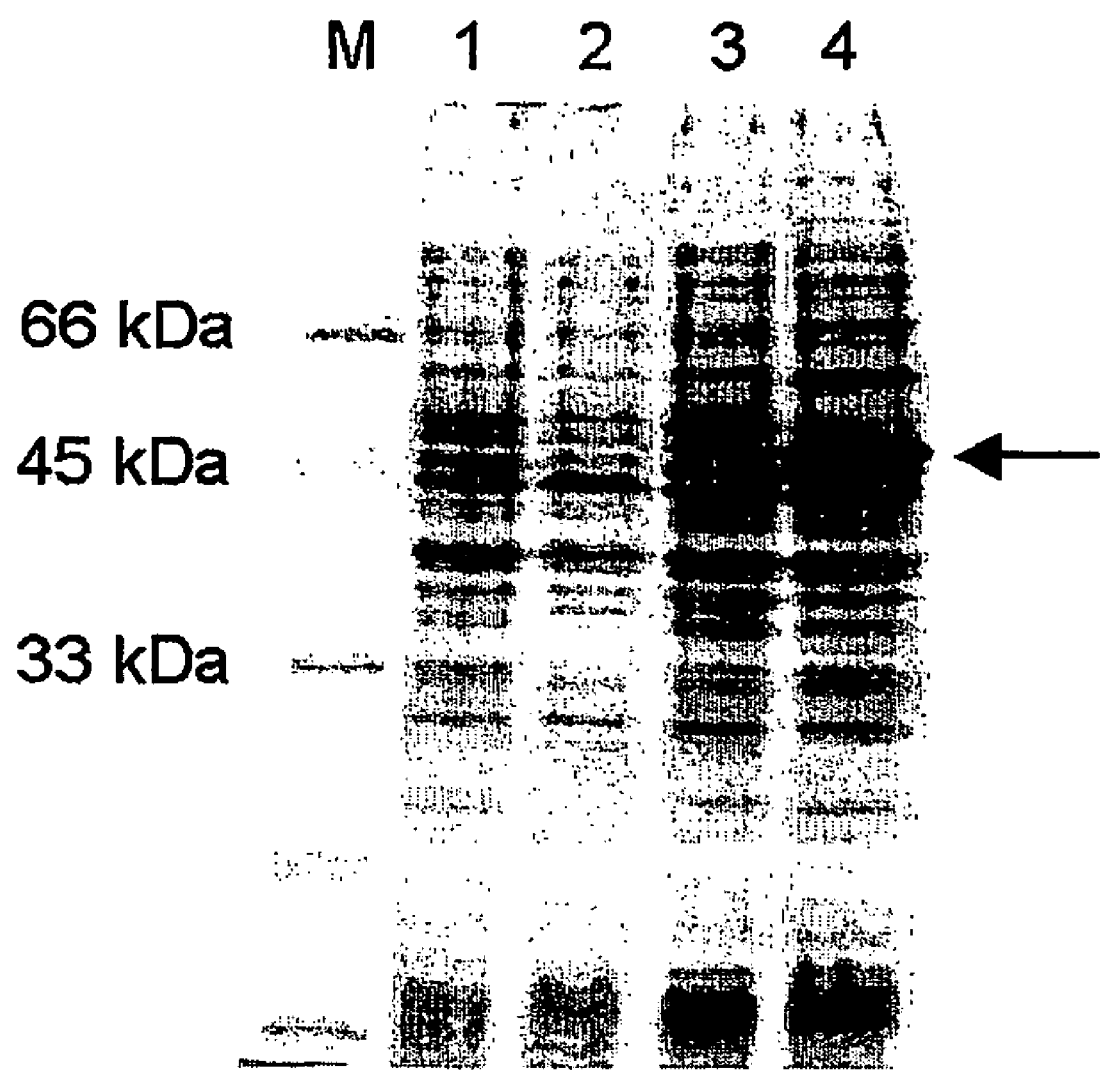
FIG. 2 depicts the analysis of the aminopeptidase derived from *Bacillus licheniformis* and expressed from *Escherichia coli* transformant by performing SDS-polyacrylamide gel electrophoresis.

Hereinafter, the present invention will be illustrated more clearly as follows.

The aminopeptidase of the present invention is identified to have enzymatic activities in a polypeptide state before signal peptide is not deleted (the sequence composed of 1st amino acid through 30th amino acid in SEQ. ID NO: 1) and after signal peptide is deleted. Although some amino acids at the amino terminus and at the carboxy terminus are cut in addition to the deletion of signal peptide, the enzymatic activities are maintained. Therefore, the aminopeptidase containing the amino acid sequence of SEQ. ID NO: 1 as well as the aminopeptidases deleted partially at the amino terminus or at the carboxy terminus from the amino acid sequence of SEQ. ID NO: 1 can be within the scope of the present invention.

Preferably, the aminopeptidase of the present invention is selected from a group of aminopeptidases having a deletion at the amino terminus of SEQ ID NO:1 wherein said amino acid sequence is selected from the group consisting of: an amino acid sequence having a deletion of amino acids 1 through 30 of SEQ. ID NO: 1; an amino acid sequence having a deletion of amino acids 1 through 39 of SEQ. ID NO: 1; an amino acid sequence having a deletion of amino acids 1 through 40 of SEQ. ID NO: 1; an amino acid sequence having a deletion of amino acids 1 through 41 of SEQ. ID NO: 1; and an amino acid sequence having a deletion of amino acids 1 through 42 of SEQ. ID NO: 1. More preferably, the aminopeptidase of the present invention has a deletion of amino acids 1 through 30 of SEQ. ID NO: 1.

Preferably, the aminopeptidase of the present invention has the amino acid sequence of SEQ. ID NO: 1 having a deletion of amino acids 444 through 449 at the carboxy terminus.

More preferably, the aminopeptidase has the amino acid sequence of SEQ ID NO: 1 having a deletion of amino acids 1 through 42 and 444 through 449.

The genes of the present invention encoding the aminopeptidase derived from *Bacillus licheniformis* can include the gene encoding amino acid sequence of SEQ. ID NO: 1, the gene encoding all of the deleted form of aminopeptidase mentioned above and the gene of SEQ. ID NO: 2.

In order to investigate functions and enzymatic activities of the aminopeptidase, the following procedure is accomplished by using the protein containing the amino acid sequence of SEQ. ID NO: 1, its genes and its polypeptide in a deleted form respectively.

In order to elucidate polypeptides having enzymatic activities of the aminopeptidase derived from *Bacillus licheniformis*, a gene encoding the aminopeptidase is cloned from the chromosomal DNA of *Bacillus licheniformis*. Concretely, for cloning genes, polypeptides having the enzymatic activities of the aminopeptidase derived from *Bacillus licheniformis* are purified, digested with trypsin so as to collect a number of peptide fragments and then determined the amino acid sequences. The information of the amino acid sequences is exploited to synthesize oligonucleotides for use of primers and then DNA fragments corresponding to a part of the aminopeptidase gene are amplified. Afterward, by utilizing these DNA fragments for probes, the aminopeptidase gene can be found from the chromosomal library derived from *Bacillus licheniformis*.

The genes of aminopeptidase observed above are examined to determine the nucleotide sequences with the DNA sequence analyzer as shown in SEQ. ID NO: 2, and the deduced DNA sequence from the genetic information of SEQ. ID NO: 1 is identified to have exactly the same amino acid sequence of the aminopeptidase purified from natural host cells. As a result, the aminopeptidase polypeptide obtained according to the present invention is screened by using data base for genetic informations and this gene is identified a novel DNA sequence that have never reported and have a enzymatic activities of the aminopeptidase when it is expressed in recombinant microbes.

Then, the matured aminopeptidase is also detected to be digested partially. In order to investigate the composition of the aminopeptidase at the carboxy terminus, the aminopeptidase purified from the recombinant bacterial transformant and the aminopeptidase purified from natural host cells, *Bacillus licheniformis,* are examined to determine molecular weights with mass spectrometry. Consequently, in both cases 6 amino acid residues are verified to be cut from the carboxy terminus.

The aminopeptidase according to the present invention is confirmed to become mature that the aminopeptidase were expressed in the cell and then, the signal peptide was deleted at the amino terminus during the extracellular secretion. Besides, the matured aminopeptidase is also digested partially.

Hence, the aminopeptidase polypeptide according to the present invention maintains enzymatic activities with presence of the signal peptide and even partially being cut at the amino terminus or at the carboxy terminus with absence of the signal peptide.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Cloning of aminopeptidase gene derived from *Bacillus licheniformis*

(1-1) Partial determination of amino acid sequence in aminopeptidase purified from *Bacillus licheniformis*

The present inventors have performed the procedure as follows in order to purify aminopeptidase protein from *Bacillus licheniformis.*

Sterilized media containing tryptone 10 g, yeast extract 5 g, NaCl 10 g per 1 L were prepared in flasks and *Bacillus licheniformis* KCTC 3058 strain was inoculated so as to be cultivated for seed-culture at 40° C., 120 rpm for about 16 hours. The seed culture broth obtained above was inoculated again to new media and cultivated at 40° C., 200–400 rpm agitation, more than 30 of dissolved oxygen. Then, the concentrations of glucose were measured with an hour interval and the cultivation was completed when the activity of aminopeptidase reached more than 35 U/ml. In order to cultivate cells, culture broth containing peptone 2 kg, yeast extract 6 kg, potassium phosphate 4 kg, NaCl 1 kg, SAG, $MgSO_4 \cdot 7H_2O$ 15 g, $FeSO_4 \cdot 7H_2O$ 1.53 g, $ZnSO_4 \cdot 7H_2O$ 1.53 g, $MnSO_4$ 1.53 g, and glucose 10 kg per distilled water 200 L in 400 L fermentor was prepared in a sterilized state. After the cultivation was completed, continuous centrifuge was utilized to remove cell debris and recovered the supernatants. The supernatant obtained above was concentrated with a concentrator and then $ZnSO_4$ was added to reach about 0.3 mM. Through 3 steps of column chromatography, aminopeptidase was purified from the concentrated solution. As a chromatography, SP-Sepharose FF, Sephacryl S-200, and DEAE-Sepharose FF were utilized in turns. The aminopeptidase purified by using the above procedure was identified to have more than 95% of purity when analyzed with the reverse phase high pressure chromatography.

The resulted aminopeptidase was precipitated by using 10% trichloroacetic acid (TCA), washed with acetone and dried. The dried protein precipitate was dissolved with 8 M urea and 0.4 M ammonium bicarbonate and treated with dithiothreitol(DTT) and iodoacetamide in turns so that disulfide bonds in the aminopeptidase were cleaved. The treated sample was dissolved again in distilled water, added about 0.05 mg of trypsin per 2 mg of aminopeptidase and treated at 37° C. for about 8 hours. The sample treated with trypsin was injected into the reverse phase high pressure chromatography (RP-HPLC) and collected to fractions of major peptide peaks. In the reverse phase chromatography, Vydac C18 reverse phase column was adopted and a linear concentration gradient using solvent A (highly purified water containing 0.05% trifluoroacetic acid(TFA)) and solvent B (highly purified water containing 0.05% TFA and 80% acetonitrile) was applied. At this moment, the analysis was performed in 0.5 ml/min of flow velocity and chromatogram was obtained by UV absorbance at 214 nm. Through this procedure, more than 10 peaks were obtained. The resulted peptide sample was analyzed with a mass spectrometry respectively and peptides composed of more than 15 amino acids were selected. The selected sample was determined the amino acid sequence with the amino acid sequence analyzer. FIG. 1 depicted the amino acid sequence of the selected peptide by using 1 character denoting an amino acid. Each peptide was numbered in orders arbitrarily in accordance with elution time through reverse phase chromatography and the arrow part depicted in FIG. 1 was used to give information for synthesizing the primers of oligonucleotides. The sample denoted as T4 among these peptide samples were deduced to contain 2 different peptides coincidently since 2 amino acids appeared at the same time in each cycle by performing the sequence analysis of amino acids. Besides, among these peptide samples, the same sequence of amino acids is contained in between T6 and T9, T11 and T13 and T16 and T17. Precisely, T4 described in SEQ. ID NO: 4 and 5, T6 in SEQ. ID NO: 6, T7 in SEQ. ID NO: 7, T9 in SEQ. ID NO: 8, T11 in SEQ. ID NO: 9, T13 in SEQ. ID NO: 10, T16 in SEQ. ID NO: 11, T17 in SEQ. ID NO: 12 respectively, which is disclosed in Sequence List independently.

(1-2) Cloning of aminopeptidase gene and determination of nucleotide sequence

By using the peptide information elucidated in Example 1(1-1), oligonucleotide primers for PCR of aminopeptidase genes were synthesized. Precisely, 5'- upstream primer (LAP-5) described in SEQ. ID NO: 13 and 3'-downstream primer(LAP-3) described in of SEQ. ID NO: 14 were utilized, which were manufactured by using the amino acid sequences described in SEQ. ID NO: 15 and SEQ. ID NO: 16 among amino acid sequences determined in Example 1 (1-1). PCR was performed 32 times repeatedly with the DNA thermal cycler; denaturation at 94° C. for 30 seconds, annealing at 40° C. for 45 seconds, and extension at 72° C. for 1 minute and chromosomal DNA of *Bacillus lichenifor-*

*mis* was used as a template. As a result, DNA fragment with about 390 bp size was obtained.

In the meantime, genomic DNA of *Bacillus licheniformis* was made by exploiting Murray and Thompson's method and digested partially with the restriction enzyme Sau3A and separated it through 0.8% agarose gel then isolated the DNA fragments corresponding to 2~3 kb. The DNA fragment was ligated into λ ZAP expression vector (Stratagene, LaJolla, USA) digested with BamHI and added to packaging extract. Then, the packaging mixture was transferred to *E. coli* XL-1 Blue MRF'. This library filter prepared above was screened by using $^{32}$P-labelled PCR fragment and detected for clones containing aminopeptidase gene. As a result, the selected clone was verified to include DNA insert with about 2.6 kb size and named it "LAP 132" clone.

The nucleotide sequence of LAP 132 was analyzed and the result was described in SEQ. ID NO: 2. In detail, it was composed of ATG initiation codon starting at 192 nucleotide and TAA termination codon at 1,539 and contained 1,347 bp ORF (open reading frame) as shown in SEQ. ID NO: 2 and in SEQ. ID NO: 3. The nucleotide was identified to encode 449 amino acids. The amino acid sequence encoded from the nucleotide sequence information elucidated above, were identical completely with the result determined by the amino acid sequence analysis of peptide fragments derived from aminopeptidase purified above. The domain of amino terminus of the aminopeptidase according to the present invention contained hydrophobic amino acid residues contiguous to cationic amino acid residues, which was similar to the signal sequence needed for the secretion. Thus, the aminopeptidase was deduced to be digested in between 30th alanine and 31st alanine when secreted. But, in Korean Patent Laid-open No. 1998-071239, the aminopeptidase was disclosed that amino terminus mainly starts from amino acid sequences described in SEQ. ID NO: 17 and heterogeneous type forms of aminopeptidases of which their cleaved sites are somewhat different with the present invention. This difference was deduced to be provoked by digesting with the other extracellular protease after the aminopeptidase was secreted from original strains. The aminopeptidase according to the present invention was compared in the amino acid sequence with other aminopeptidase recorded in Genebank by using BLAST searching. As a result, it was shown to have 62% homology with the aminopeptidase derived from *Bacillus subtilis,* and 58% homology with aminopeptidase derived from *Bacillus halodurans.* The aminopeptidase according to the present invention identified as a new aminopeptidase not reported previously.

The inventors of the present invention have transformed the aminopeptidase gene, "LAP 132" derived from *Bacillus licheniformis,* into *E. coli* XLOLR strain and have named with "*E. coli* XLOLR/LAP 132". They have deposited with International Deposit Organization, the Korean Collection for Type Cultures (KCTC) of the Korean Research Institute of Bioscience and Biotechnology (KRIBB), Republic of Korea on Apr. 26, 2001, and identified as accession number, KCTC 1000 BP.

Example 2

Gene expression of aminopeptidase in *Escherichia coli* transformant

The aminopeptidase gene cloned according to the present invention was subcloned into the expression vector pBK-CMV (Stratagene, USA) and named the expression vector "pLAP32" so as to be used as a source of aminopeptidase gene. Then, the PCR fragment with about 1.2 kb size containing a region encoding aminopeptidase was subcloned into the vector pET11a (Stratagene, USA) and named the expression vector pETLAP45. The expression vector was transformed into *E. coli* BL21(DE3) and exploited it to express a fused protein attaching His-tag peptide. The expression of aminopeptidase in the expression system described above was verified by performing SDS-PAGE. As illustrated in FIG. 2, the molecular weight of aminopeptidase was examined to reach about 45 kDa onto SDS-PAGE and identical to that deduced from its gene. In FIG. 2, lane M depicted a standard marker of molecular weights; lane 1, *E. coli* transformed into the expression vector pET11a (not inducing the expression); lane 2, *E. coli* transformed into the expression vector pET11a (inducing the activation of T7 promoter); lane 3, *E. coli* transformed into the expression vector pETLAP45 (not included the expression); and lane 4, *E. coli* transformed into the expression vector pETLAP45 (inducing the activation of T7 promoter). The arrow depicted in FIG. 2 denoted the aminopeptidase.

The inventors of the present invention have tried to detect enzymatic activities of aminopeptidase secreted from *E. coli* transformant after expression the gene. Above all, when the *E. coli* transformant was sonicated and analyzed, the enzymatic activities of the aminopeptidase from the *E. coli* transformant were found in soluble fractions. As a result, the aminopeptidase according to the present invention was identified to have the same size with that deduced from the gene and to show the enzymatic activities.

Example 3

Figure 3:
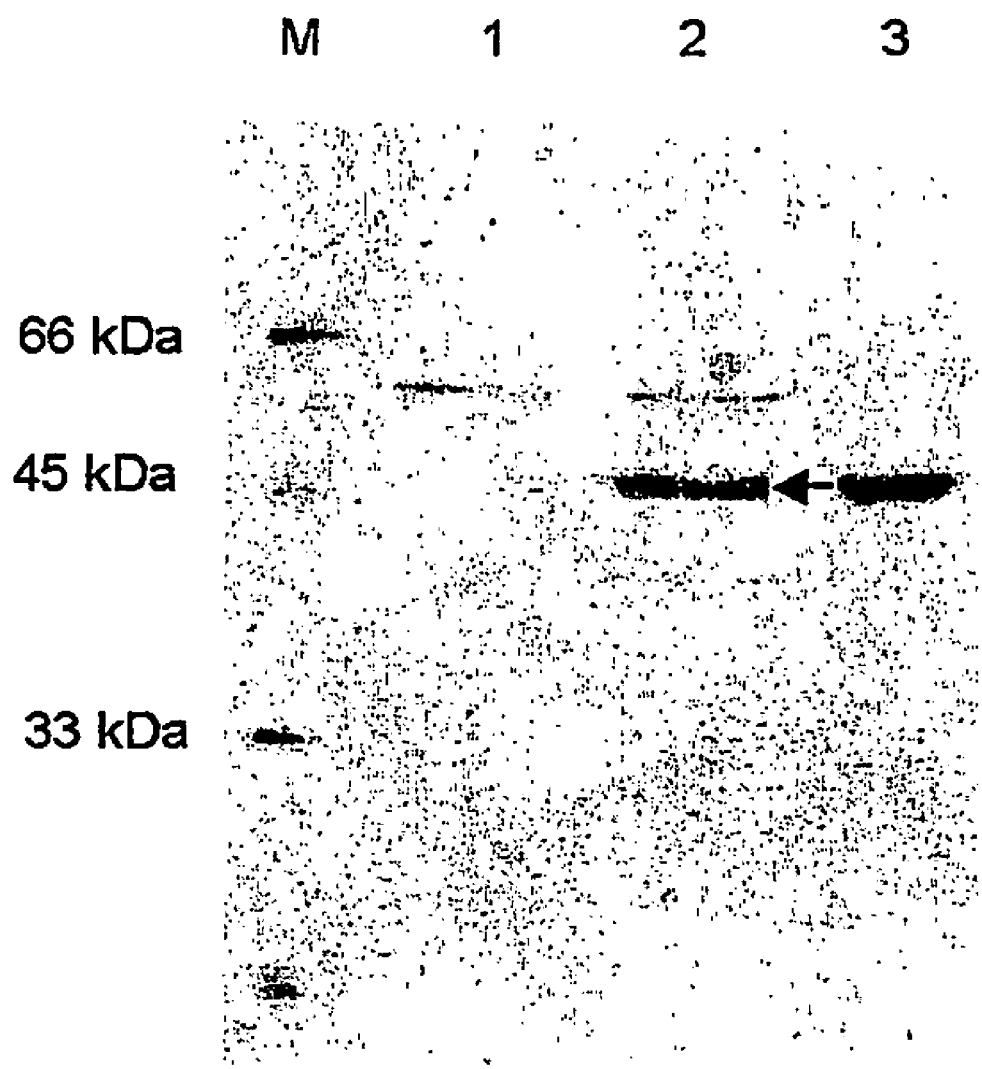
FIG. 3 depicts the analysis of the aminopeptidase derived from *Bacillus licheniformis* and expressed from *Bacillus subtilis* transformant by performing SDS-polyacrylamide gel electrophoresis.

Gene expression of aminopeptidase in *Bacillus Subtilis* transformant, sequence analysis of the purified aminopeptidase at the amino terminus and determination of its molecular weight (3-1) Gene expression of aminopeptidase in *Bacillus licheniformis* transformant In the present invention, DNA fragment digested with HindIII-SacI, containing a region encoding aminopeptidase as well as promoter, 3'-untranslated region, having about 2.6 kb size and was subcloned into the *Bacillus* vector pRB373 and the resulted expression vector was named pRB373-LAP. The expression vector was transformed into *Bacillus subtilis,* and cultivated and then the cultured broth was analyzed by using SDS-PAGE. The aminopeptidase was observed to be secreted from the cultured solution and to have about 45 kDa of molecular weight, which was compatible with that from *Bacillus licheniformis* (See FIG. 3). In FIG. 3, lane M depicted a standard marker of molecular weight; lane 1, *Bacillus subtilis* transformed into the expression vector pRB373; lane 2, *Bacillus subtilis* transformed into the expression vector pRB373-LAP; and lane 3, aminopeptidase purified from *Bacillus licheniformis.* The arrow depicted in FIG. 3 denoted the aminopeptidase.

(3-2) Sequence analysis of the aminopeptidase polypeptide at the amino terminus expressed from *Bacillus subtilis* transformant In order to purify the aminopeptidase, recombinant *Bacillus subtilis* transformant containing the gene according to the present invention was cultivated and the cultured broth was separated by performing SP-Sepharose chromatography. The amino acid sequence at the amino terminus of the purified aminopeptidase was determined by the amino acid analyzer. As a result, it was verified that the sequence of aminopeptidase at the amino terminus was heterogeneous as found in the aminopeptidase derived from natural host cells and initiated with SEQ. ID NO: 17 mostly among those with SEQ. ID NO: 18. And the aminopeptidase initiated with Asn, Val and Glu also existed.

(3-3) Determination of molecular weight in aminopeptidase polypeptide expressed from recombinant *Bacillus subtilis* transformant The recombinant *Bacillus subtilis* transformant containing the aminopeptidase gene was cultivated and the cultured broth was exploited to purify the aminopeptidase by using SP-Sepharose chromatography. The molecular weight of the aminopeptidase was examined with mass spectrometry and as a result, substances corresponding to 42,965 Da of molecular weight, 43,241 Da and 43,468 Da appeared. This result was compared with that obtained from the sequence analysis of amino acids in Example 3(3-2) and additional 6 amino acids was deduced to be removed at the carboxy terminus. That is to say, the polypeptide described in SEQ. ID NO: 1, the amino terminus started from SEQ. ID NO: 17 and the carboxy terminus ended to SEQ. ID NO: 19 had a theoretical molecular weight corresponding to about 43,241 Da. Then, another polypeptide added in 2 amino acids from the above had a molecular weight corresponding to 43,468 Da and the other polypeptide deleted in 2 amino acids had a molecular weight corresponding to 42,965 Da, which was identical to the results obtained from mass spectrometry exactly.

In the meantime, the aminopeptidase purified from a natural host cell, *Bacillus licheniformis* was examined by using mass spectrometry through the same procedure of Example 1 (1-1) and the same result with that of recombinant transformant was obtained.

Example 4

Activity measurement of aminopeptidase and its deleted forms expressed in recombinant *E. coli* transformant and *Bacillus subtilis* transformant The inventors of the present invention measured the aminopeptidase activity using cell lysate solution sonicated in case of recombinant *E. coli* transformant and using cultured solution obtained in Example 3 (3-1) in case of recombinant *Bacillus subtilis* transformant.

Concretely, Pflleiderer's method was utilized in order to estimate enzymatic activities of the aminopeptidase produced in Example 2 and Example 3 (Pflleiderer, *Meth. Enzymol.*, 1970, 19, 514–521). 50 µl of cultured solution was added into the mixture of 1 M Tris (pH 8.5)(950 µl), and 0.1 M leucine-p-nitroanilide(20 µl) in DMSO, reacted for 3 minutes at 60° C., added 100 µl of 70% acetic acid, ended the reaction and detected the absorbance at 405 nm.

Figure 4:
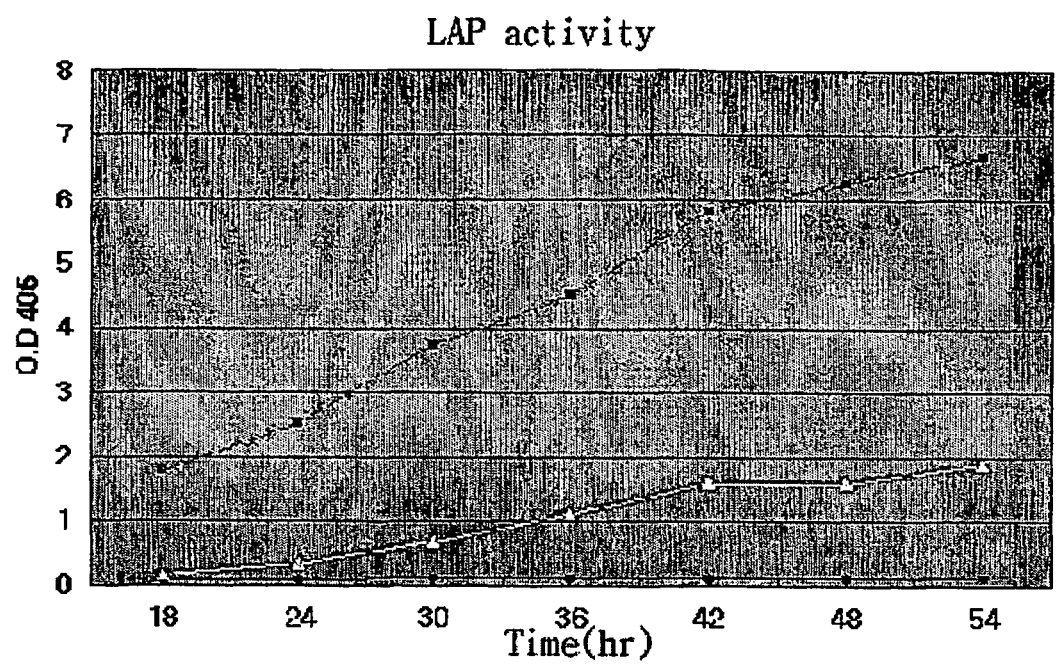
FIG. 4 depicts the examination of enzymatic activities in the aminopeptidase derived from *Bacillus licheniformis* and expressed from *Bacillus subtilis* transformant schematically.

Consequently, as shown in FIG. 4, there was a precise difference in between *Bacillus subtilis* strain transformed with the aminopeptidase gene and *Bacillus subtilis* strain containing the expression vector. In addition, the aminopeptidase purified from recombinant *Bacillus subtilis* was composed conincidently of deleted forms at the amino terminus or at the carboxy terminus as demonstrated in Example 3 (3-2) and (3-3) and the samples were also identified to have enzymatic activities. In FIG. 4, □ depicted pRB373-LAP, *Bacillus subtilis* transformed with the expression vector containing the aminopeptidase gene; Δ depicted LG, *Bacillus subtilis* cultivated in LB culture broth; and ♦ depicted pRB373, *Bacillus subtilis* transformed with the expression vector not containing an aminopeptidase gene.

INDUSTRIAL APPLICABILITY

As demonstrated clearly and confirmed above, according to the present invention the gene encoding the aminopeptidase derived from *Bacillus licheniformis* is cloned and expressed by using recombinant bacterial transformant and is identified to be novel gene not reported previously. The aminopeptidase purified and elucidated according to the present invention can be exploited usefully to manufacture natural type recombinant proteins as well as applied to other enzymatic reactions widely.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. An isolated aminopeptidase having the amino acid sequence set forth in SEQ ID NO:1.

2. An isolated aminopeptidase having an amino acid sequence selected from the group consisting of,
   the sequence of amino acids from position 31 through position 449 of SEQ ID NO:1;
   the sequence of amino acids from position 40 through position 449 of SEQ ID NO:1;
   the sequence of amino acids from position 41 through position 449 of SEQ ID NO:1; and
   the sequence of amino acids from position 42 through position 449 of SEQ ID NO:1.

3. An isolated aminopeptidase consisting of the sequence of amino acids from position 1 through position 443 of SEQ ID NO:1.

4. An isolated aminopeptidase having an amino acid sequence selected from the group consisting of,
   the sequence of amino acids from position 31 through position 443 of SEQ ID NO:1;
   the sequence of amino acids from position 40 through position 443 of SEQ ID NO:1;
   the sequence of amino acids from position 41 through position 443 of SEQ ID NO:1; and
   the sequence of amino acids from position 42 through position 443 of SEQ ID NO:1.

5. An isolated nucleic acid sequence encoding an aminopeptidase according to claim 1, 2, 3, or 4.

6. The expression vector pLAP132 which comprises the nucleotide sequence set forth in SEQ ID NO:2.

7. An *Escherichia coli* transformant XLOR/LAP132 transformed with the expression vector pLAP132 and having the accession number KCTC 1000 BP.

8. A process for preparing a peptide or a recombinant protein lacking a methionine present at its native amino-terminus that comprises the following steps:
   (1) purifying the peptide or recombinant protein containing a methionine-x-proline sequence at the amino terminus wherein the x of said methionine-x-proline sequence is any amino acid;
   (2) contacting said purified peptide or recombinant protein with an aminopeptidase of any of claim 1, 2, 3, or 4 under conditions suitable for cleavage of the amino-terminal methionine from the recombinant protein; and
   (3) thereby obtaining said peptide or recombinant protein having an amino-terminus lacking a methionine.

* * * * *

SEQUENCE LISTING

```
<160> NUMBER OF SEQ ID NOS: 19

<210> SEQ ID NO 1
<211> LENGTH: 449
<212> TYPE: PRT
<213> ORGANISM: Bacillus licheniformis
<220> FEATURE:
<221> NAME/KEY: SIGNAL
<222> LOCATION: (1)..(30)
<220> FEATURE:
<221> NAME/KEY: DOMAIN
<222> LOCATION: (133)..(211)
<223> OTHER INFORMATION: PA (Protease associated) domain
<220> FEATURE:
<221> NAME/KEY: DOMAIN
<222> LOCATION: (261)..(308)
<223> OTHER INFORMATION: Peptidase family M20/M25/M40
```

```
<400> SEQUENCE: 1

Met Lys Arg Lys Met Met Met Ile Gly Leu Ala Leu Ser Val Ile Ala
  1               5                  10                  15

Gly Gly Val Phe Ala Ala Gly Thr Gly Asn Ala Val Gln Ala Pro
             20                  25                  30

Gln Glu Thr Ala Ile Ala Lys Asn Val Glu Lys Phe Ser Lys Lys Phe
         35                  40                  45

Asn Glu Asn Arg Ala Tyr Gln Thr Ile Tyr His Leu Ser Glu Thr Val
         50                  55                  60

Gly Pro Arg Val Thr Gly Thr Ala Glu Lys Lys Ser Ala Ala Phe
 65              70                  75                  80

Ile Ala Ser Gln Met Lys Lys Ser Asn Leu Lys Val Thr Thr Gln Thr
                 85                  90                  95

Phe Ser Ile Pro Asp Arg Leu Glu Gly Thr Leu Thr Val Gln Gly Asn
                100                 105                 110

Asn Val Pro Ser Arg Pro Ala Gly Ser Ala Pro Thr Ala Ala Glu
             115                 120                 125

Gly Leu Ala Ala Pro Leu Tyr Asp Ala Gly Leu Gly Leu Pro Gly Asp
130                 135                 140

Phe Thr Glu Glu Ala Arg Gly Lys Ile Ala Val Ile Leu Arg Gly Glu
145                 150                 155                 160

Leu Thr Phe Tyr Glu Lys Ala Lys Asn Ala Ala Asp Ala Gly Ala Ser
                165                 170                 175

Gly Val Ile Ile Tyr Asn Asn Val Asp Gly Leu Val Pro Leu Thr Pro
                180                 185                 190

Asn Leu Ser Gly Asn Lys Val Asp Val Pro Val Gly Val Lys Lys
             195                 200                 205

Glu Asp Gly Glu Lys Leu Leu Ser Glu Gln Glu Ala Ile Leu Lys Leu
210                 215                 220

Lys Ala His Lys Asn Gln Thr Ser Gln Asn Val Ile Gly Val Arg Lys
225                 230                 235                 240

Ala Lys Gly Val Lys Asn Pro Asp Ile Val Tyr Val Thr Ser His Tyr
                245                 250                 255

Asp Ser Val Pro Tyr Ala Pro Gly Ala Asn Asp Asn Ala Ser Gly Thr
             260                 265                 270

Ser Val Val Leu Glu Leu Ala Arg Ile Met Lys Thr Val Pro Ala Asp
     275                 280                 285

Lys Glu Ile Arg Phe Ile Thr Phe Gly Ala Glu Ile Gly Leu Leu
290                 295                 300

Gly Ser Arg His Tyr Val Ser Thr Leu Ser Glu Gln Glu Val Lys Arg
305                 310                 315                 320

Ser Val Ala Asn Phe Asn Leu Asp Met Val Ala Thr Ser Trp Glu Asn
                325                 330                 335

Ala Ser Gln Leu Tyr Ile Asn Thr Pro Asp Gly Ser Ala Asn Leu Val
             340                 345                 350

Trp Gln Leu Ser Lys Ala Ser Leu Ser Leu Gly Lys Asp Val Leu
             355                 360                 365

Phe Leu His Gln Gly Gly Ser Ser Asp His Val Pro Phe His Glu Ala
370                 375                 380

Gly Ile Asp Ser Ala Asn Phe Ile Trp Arg Glu Pro Gly Thr Gly Ala
385                 390                 395                 400

Leu Glu Pro Trp Tyr His Thr Pro Tyr Asp Thr Ile Glu His Ile Ser
                405                 410                 415
```

-continued

```
Lys Asp Arg Leu Lys Thr Ala Gly Gln Ile Ala Gly Thr Ala Val Tyr
            420                 425                 430

Asn Leu Thr Lys Lys Glu Asn Arg Thr Pro Ser Tyr Ser Ser Val Ala
        435                 440                 445

Gln

<210> SEQ ID NO 2
<211> LENGTH: 2052
<212> TYPE: DNA
<213> ORGANISM: Bacillus licheniformis
<220> FEATURE:
<221> NAME/KEY: RBS
<222> LOCATION: (179)..(184)
<223> OTHER INFORMATION: RBS candidate 1
<220> FEATURE:
<221> NAME/KEY: RBS
<222> LOCATION: (195)..(200)
<223> OTHER INFORMATION: RBS candidate 2
<220> FEATURE:
<221> NAME/KEY: CDS
<222> LOCATION: (192)..(1538)
<223> OTHER INFORMATION: CDS candidate 1
<220> FEATURE:
<221> NAME/KEY: mat_peptide
<222> LOCATION: (282)..(1538)
<220> FEATURE:
<221> NAME/KEY: sig_peptide
<222> LOCATION: (192)..(281)

<400> SEQUENCE: 2
gatcctgata attcggacgt attctaaaca gaaaaaaggc tcacgtcaag catcctatta      60
aacaaaaaaa cttttttatc aaacttcaaa ttactggtct atcgaatcat ttatcagatg    120
catgcaggat tcacccgctc agctgcgaat atctcttctc aggaaaacaa gaccatcaag    180
gaggtttatg t            atg aag aga aaa atg atg atg atc gga ttg gcg    224
                        Met Lys Arg Lys Met Met Met Ile Gly Leu Ala
                          1               5                  10 cta tcc gta ata gca ggc ggc gtg ttc gcc gct gga acg ggg aat gct       272
Leu Ser Val Ile Ala Gly Gly Val Phe Ala Ala Gly Thr Gly Asn Ala
             15                  20                  25 gtt caa gcg gcg cct cag gaa aca gcc atc gca aaa aat gtc gaa aaa       320
Val Gln Ala Ala Pro Gln Glu Thr Ala Ile Ala Lys Asn Val Glu Lys
         30                  35                  40 ttc agc aaa aaa ttc aat gaa aac cgc gcc tat caa acg att tac cat       368
Phe Ser Lys Lys Phe Asn Glu Asn Arg Ala Tyr Gln Thr Ile Tyr His
     45                  50                  55 tta agc gaa acg gtc gga ccg cgt gtg aca ggc acg gcg gaa gaa aaa       416
Leu Ser Glu Thr Val Gly Pro Arg Val Thr Gly Thr Ala Glu Glu Lys
 60                  65                  70                  75 aag agc gcc gct ttc atc gcc tca cag atg aaa aaa tca aat ctg aaa       464
Lys Ser Ala Ala Phe Ile Ala Ser Gln Met Lys Lys Ser Asn Leu Lys
                 80                  85                  90 gtg acc aca caa acc ttc agc ata cct gac cgg ctg gaa gga acg ctt       512
Val Thr Thr Gln Thr Phe Ser Ile Pro Asp Arg Leu Glu Gly Thr Leu
             95                 100                 105 acc gtt cag gga aat aac gtg cct tcg cgg cct gcc gcc ggt tcc gcc       560
Thr Val Gln Gly Asn Asn Val Pro Ser Arg Pro Ala Ala Gly Ser Ala
         110                 115                 120 ccg aca gca gca gaa ggc ctg gcc gct cct ctc tat gat gcc ggc ctc       608
Pro Thr Ala Ala Glu Gly Leu Ala Ala Pro Leu Tyr Asp Ala Gly Leu
     125                 130                 135 ggc ctg cct ggc gac ttc acc gag gaa gcg aga ggc aaa atc gcc gtc       656
Gly Leu Pro Gly Asp Phe Thr Glu Glu Ala Arg Gly Lys Ile Ala Val
```

-continued

| | |
|---|---|
| att tta aga ggc gag ctg aca ttc tat gaa aaa gcg aaa aac gct gct<br>Ile Leu Arg Gly Glu Leu Thr Phe Tyr Glu Lys Ala Lys Asn Ala Ala<br>140                   160                   165                   170 | 704 |
| gac gca ggc gca agc gga gtg atc att tat aat aac gtc gac ggt ctc<br>Asp Ala Gly Ala Ser Gly Val Ile Ile Tyr Asn Asn Val Asp Gly Leu<br>               175                   180                   185 | 752 |
| gtc cct ctg act ccg aat ctc agc ggt aat aaa gtc gat gtt ccg gta<br>Val Pro Leu Thr Pro Asn Leu Ser Gly Asn Lys Val Asp Val Pro Val<br>           190                   195                   200 | 800 |
| gtc ggc gtc aaa aag gaa gac gga gaa aag ctg ctt tct gaa caa gaa<br>Val Gly Val Lys Lys Glu Asp Gly Glu Lys Leu Leu Ser Glu Gln Glu<br>205                   210                   215 | 848 |
| gcg atc ttg aag ctg aag gct cat aaa aat caa aca tcg caa aac gta<br>Ala Ile Leu Lys Leu Lys Ala His Lys Asn Gln Thr Ser Gln Asn Val<br>220                   225                   230                   235 | 896 |
| atc ggc gtc cgc aaa gca aaa ggt gtc aaa aat ccg gac atc gtg tat<br>Ile Gly Val Arg Lys Ala Lys Gly Val Lys Asn Pro Asp Ile Val Tyr<br>               240                   245                   250 | 944 |
| gtg act tcg cat tat gac agc gtc cct tac gct ccc gga gcc aat gac<br>Val Thr Ser His Tyr Asp Ser Val Pro Tyr Ala Pro Gly Ala Asn Asp<br>           255                   260                   265 | 992 |
| aat gcc tcc ggc act tca gtc gtt ctt gaa ctg gcc cgg atc atg aag<br>Asn Ala Ser Gly Thr Ser Val Val Leu Glu Leu Ala Arg Ile Met Lys<br>270                   275                   280 | 1040 |
| acg gtt ccg gcc gac aaa gaa att cgc ttt att aca ttc ggc gcc gaa<br>Thr Val Pro Ala Asp Lys Glu Ile Arg Phe Ile Thr Phe Gly Ala Glu<br>285                   290                   295 | 1088 |
| gaa atc ggt ctc ctc gga tcg cgc cat tat gtc agc acc ttg tca gag<br>Glu Ile Gly Leu Leu Gly Ser Arg His Tyr Val Ser Thr Leu Ser Glu<br>300                   305                   310                   315 | 1136 |
| cag gaa gtc aaa cgg agc gtt gcc aac ttt aac tta gat atg gtg gcg<br>Gln Glu Val Lys Arg Ser Val Ala Asn Phe Asn Leu Asp Met Val Ala<br>               320                   325                   330 | 1184 |
| aca agc tgg gaa aat gct tca cag ctg tac atc aat aca cct gac ggt<br>Thr Ser Trp Glu Asn Ala Ser Gln Leu Tyr Ile Asn Thr Pro Asp Gly<br>           335                   340                   345 | 1232 |
| tca gca aac ctc gtc tgg cag cta agt aaa gcc gct tct tta agc ctt<br>Ser Ala Asn Leu Val Trp Gln Leu Ser Lys Ala Ala Ser Leu Ser Leu<br>350                   355                   360 | 1280 |
| ggg aaa gac gta tta ttt tta cat caa ggc gga tca tcc gac cat gtc<br>Gly Lys Asp Val Leu Phe Leu His Gln Gly Gly Ser Ser Asp His Val<br>365                   370                   375 | 1328 |
| cca ttc cat gaa gcc ggc atc gac tca gcc aac ttc att tgg aga gag<br>Pro Phe His Glu Ala Gly Ile Asp Ser Ala Asn Phe Ile Trp Arg Glu<br>380                   385                   390                   395 | 1376 |
| ccg gga aca ggt gca ttg gag cct tgg tac cac acc cct tac gac acg<br>Pro Gly Thr Gly Ala Leu Glu Pro Trp Tyr His Thr Pro Tyr Asp Thr<br>               400                   405                   410 | 1424 |
| att gaa cac atc agc aaa gac agg ctg aaa aca gcc gga caa atc gcg<br>Ile Glu His Ile Ser Lys Asp Arg Leu Lys Thr Ala Gly Gln Ile Ala<br>           415                   420                   425 | 1472 |
| gga aca gcc gtg tat aac ctg acc aag aaa gaa aac aga aca ccg tct<br>Gly Thr Ala Val Tyr Asn Leu Thr Lys Lys Glu Asn Arg Thr Pro Ser<br>430                   435                   440 | 1520 |
| tac agc tca gtc gcc caa      ta atattaaaaa ggagcagatc gattcaatct<br>Tyr Ser Ser Val Ala Gln<br>445 | 1570 |
| gctccttttt tataccgctt cttttcaatc cttcatcagc ttaataaacc tgaagctcat | 1630 |

```
caaaacgctg ccgatggcaa ccacaatcat gaccaccccc agatcctgaa aatgacccgc   1690
ggttatttct tctccaaaca acagacccag aatgacggac gaaaagatcg agccaagata   1750
gcggcatgtt tggaagagcc ccgaagtggt tccgacgatg tccggcgggc ttgccgtaaa   1810
catggcggcc tggagggcga cattgccgag tccatagctg accccagca agagaggat    1870 gatgcctttc cacaacatcg gtgcatcgac aaaaaacaat gtgagcagga tagcgccggc   1930
tgccattaag caagaaccaa ttaaaacagg ctgcgtttca cctgaacggt caatccatgt   1990
cccgacgaaa ggcgaaatca atacgctcgt cccggacatg aacagcatca aaagacccgt   2050
cg                                                                 2052
```

<210> SEQ ID NO 3
<211> LENGTH: 449
<212> TYPE: PRT
<213> ORGANISM: Bacillus licheniformis

<400> SEQUENCE: 3

```
Met Lys Arg Lys Met Met Met Ile Gly Leu Ala Leu Ser Val Ile Ala
  1               5                  10                  15

Gly Gly Val Phe Ala Ala Gly Thr Gly Asn Ala Val Gln Ala Ala Pro
                 20                  25                  30

Gln Glu Thr Ala Ile Ala Lys Asn Val Glu Lys Phe Ser Lys Lys Phe
             35                  40                  45

Asn Glu Asn Arg Ala Tyr Gln Thr Ile Tyr His Leu Ser Glu Thr Val
         50                  55                  60

Gly Pro Arg Val Thr Gly Thr Ala Glu Glu Lys Lys Ser Ala Ala Phe
 65                  70                  75                  80

Ile Ala Ser Gln Met Lys Lys Ser Asn Leu Lys Val Thr Thr Gln Thr
                 85                  90                  95

Phe Ser Ile Pro Asp Arg Leu Glu Gly Thr Leu Thr Val Gln Gly Asn
            100                 105                 110

Asn Val Pro Ser Arg Pro Ala Ala Gly Ser Ala Pro Thr Ala Ala Glu
        115                 120                 125

Gly Leu Ala Ala Pro Leu Tyr Asp Ala Gly Leu Gly Leu Pro Gly Asp
    130                 135                 140

Phe Thr Glu Glu Ala Arg Gly Lys Ile Ala Val Ile Leu Arg Gly Glu
145                 150                 155                 160

Leu Thr Phe Tyr Glu Lys Ala Lys Asn Ala Ala Asp Ala Gly Ala Ser
                165                 170                 175

Gly Val Ile Ile Tyr Asn Asn Val Asp Gly Leu Val Pro Leu Thr Pro
            180                 185                 190

Asn Leu Ser Gly Asn Lys Val Asp Val Pro Val Val Gly Val Lys Lys
        195                 200                 205

Glu Asp Gly Glu Lys Leu Leu Ser Glu Gln Glu Ala Ile Leu Lys Leu
    210                 215                 220

Lys Ala His Lys Asn Gln Thr Ser Gln Asn Val Ile Gly Val Arg Lys
225                 230                 235                 240

Ala Lys Gly Val Lys Asn Pro Asp Ile Val Tyr Val Thr Ser His Tyr
                245                 250                 255

Asp Ser Val Pro Tyr Ala Pro Gly Ala Asn Asp Asn Ala Ser Gly Thr
            260                 265                 270

Ser Val Val Leu Glu Leu Ala Arg Ile Met Lys Thr Val Pro Ala Asp
        275                 280                 285
```

```
Lys Glu Ile Arg Phe Ile Thr Phe Gly Ala Glu Ile Gly Leu Leu
    290                 295                 300

Gly Ser Arg His Tyr Val Ser Thr Leu Ser Glu Gln Glu Val Lys Arg
305                 310                 315                 320

Ser Val Ala Asn Phe Asn Leu Asp Met Val Ala Thr Ser Trp Glu Asn
                325                 330                 335

Ala Ser Gln Leu Tyr Ile Asn Thr Pro Asp Gly Ser Ala Asn Leu Val
                340                 345                 350

Trp Gln Leu Ser Lys Ala Ala Ser Leu Ser Leu Gly Lys Asp Val Leu
            355                 360                 365

Phe Leu His Gln Gly Gly Ser Ser Asp His Val Pro Phe His Glu Ala
    370                 375                 380

Gly Ile Asp Ser Ala Asn Phe Ile Trp Arg Glu Pro Gly Thr Gly Ala
385                 390                 395                 400

Leu Glu Pro Trp Tyr His Thr Pro Tyr Asp Thr Ile Glu His Ile Ser
                405                 410                 415

Lys Asp Arg Leu Lys Thr Ala Gly Gln Ile Ala Gly Thr Ala Val Tyr
                420                 425                 430

Asn Leu Thr Lys Lys Glu Asn Arg Thr Pro Ser Tyr Ser Ser Val Ala
            435                 440                 445

Gln

<210> SEQ ID NO 4
<211> LENGTH: 11
<212> TYPE: PRT
<213> ORGANISM: Bacillus licheniformis

<400> SEQUENCE: 4

Ile Met Lys Thr Val Pro Ala Asp Lys Glu Ile
  1               5                  10

<210> SEQ ID NO 5
<211> LENGTH: 11
<212> TYPE: PRT
<213> ORGANISM: Bacillus licheniformis

<400> SEQUENCE: 5

His Tyr Val Ser Thr Leu Ser Glu Gln Glu Val
  1               5                  10

<210> SEQ ID NO 6
<211> LENGTH: 15
<212> TYPE: PRT
<213> ORGANISM: Bacillus licheniformis

<400> SEQUENCE: 6

Ala Tyr Gln Thr Ile Tyr His Leu Ser Glu Thr Val Gly Pro Arg
  1               5                  10                  15

<210> SEQ ID NO 7
<211> LENGTH: 22
<212> TYPE: PRT
<213> ORGANISM: Bacillus licheniformis

<400> SEQUENCE: 7

Thr Ala Gly Gln Ile Ala Gly Thr Ala Val Tyr Asn Leu Thr Lys Lys
  1               5                  10                  15

Glu Asn Arg Thr Pro Ser
                20
```

```
<210> SEQ ID NO 8
<211> LENGTH: 27
<212> TYPE: PRT
<213> ORGANISM: Bacillus licheniformis

<400> SEQUENCE: 8

Ala Tyr Gln Thr Ile Tyr His Leu Ser Glu Thr Val Gly Pro Arg Val
 1               5                  10                  15

Thr Gly Thr Ala Glu Glu Lys Lys Ser Ala Ala
             20                  25

<210> SEQ ID NO 9
<211> LENGTH: 19
<212> TYPE: PRT
<213> ORGANISM: Bacillus licheniformis

<400> SEQUENCE: 9

Lys Ala Lys Gly Val Lys Asn Pro Asp Ile Val Tyr Val Thr Ser His
 1               5                  10                  15

Tyr Asp Ser

<210> SEQ ID NO 10
<211> LENGTH: 20
<212> TYPE: PRT
<213> ORGANISM: Bacillus licheniformis

<400> SEQUENCE: 10

Gly Val Lys Asn Pro Asp Ile Val Tyr Val Thr Ser His Tyr Asp Ser
 1               5                  10                  15

Val Pro Tyr Ala
             20

<210> SEQ ID NO 11
<211> LENGTH: 20
<212> TYPE: PRT
<213> ORGANISM: Bacillus licheniformis

<400> SEQUENCE: 11

Phe Ile Thr Phe Gly Ala Glu Glu Ile Gly Leu Leu Gly Ser Arg His
 1               5                  10                  15

Tyr Val Ser Thr
             20

<210> SEQ ID NO 12
<211> LENGTH: 20
<212> TYPE: PRT
<213> ORGANISM: Bacillus licheniformis

<400> SEQUENCE: 12

Ala Ala Ser Leu Ser Leu Gly Lys Asp Val Leu Phe Leu His Gln Gly
 1               5                  10                  15

Gly Ser Ser Asp
             20

<210> SEQ ID NO 13
<211> LENGTH: 18
<212> TYPE: DNA
<213> ORGANISM: Artificial Sequence
<220> FEATURE:
<223> OTHER INFORMATION: LAP-5 upstream primer
<220> FEATURE:
<221> NAME/KEY: misc_feature
<222> LOCATION: (1)..(18)
```

```
<223> OTHER INFORMATION: n equals A, T, G, or C

<400> SEQUENCE: 13
aayccngaya thgtntay                                              18

<210> SEQ ID NO 14
<211> LENGTH: 18
<212> TYPE: DNA
<213> ORGANISM: Artificial Sequence
<220> FEATURE:
<223> OTHER INFORMATION: LAP-3 downstream primer
<220> FEATURE:
<221> NAME/KEY: misc_feature
<222> LOCATION: (1)..(18)
<223> OTHER INFORMATION: n equals A, T, G, or C

<400> SEQUENCE: 14
raanagnacr tcyttncc                                              18

<210> SEQ ID NO 15
<211> LENGTH: 6
<212> TYPE: PRT
<213> ORGANISM: Bacillus licheniformis

<400> SEQUENCE: 15

Asn Pro Asp Ile Val Tyr
 1               5

<210> SEQ ID NO 16
<211> LENGTH: 7
<212> TYPE: PRT
<213> ORGANISM: Bacillus licheniformis

<400> SEQUENCE: 16

Gly Lys Asp Val Leu Phe Leu
 1               5

<210> SEQ ID NO 17
<211> LENGTH: 5
<212> TYPE: PRT
<213> ORGANISM: Bacillus licheniformis

<400> SEQUENCE: 17

Lys Phe Ser Lys Lys
 1               5

<210> SEQ ID NO 18
<211> LENGTH: 8
<212> TYPE: PRT
<213> ORGANISM: Bacillus licheniformis

<400> SEQUENCE: 18

Asn Val Glu Lys Phe Ser Lys Lys
 1               5

<210> SEQ ID NO 19
<211> LENGTH: 5
<212> TYPE: PRT
<213> ORGANISM: Bacillus licheniformis

<400> SEQUENCE: 19

Asn Arg Thr Pro Ser
 1               5
```